United States Patent [19]
Runge

[11] Patent Number: 5,743,845
[45] Date of Patent: Apr. 28, 1998

[54] BIVENTRICULAR PULSATILE CARDIAC SUPPORT SYSTEM HAVING A MECHANICALLY BALANCED STROKE VOLUME

[76] Inventor: Thomas M. Runge, P.O. Box 50045, Austin, Tex. 78763

[21] Appl. No.: 371,964

[22] Filed: Jan. 12, 1995

[51] Int. Cl.$^6$ .................................. A61M 1/10
[52] U.S. Cl. .................................. 600/16
[58] Field of Search .................. 600/16, 17, 18

[56] References Cited

U.S. PATENT DOCUMENTS

| | | |
|---|---|---|
| 3,518,033 | 6/1970 | Anderson . |
| 3,585,648 | 6/1971 | Suroff . |
| 3,679,331 | 7/1972 | Kushner . |
| 4,080,958 | 3/1978 | Bregman . |
| 4,143,425 | 3/1979 | Runge . |
| 4,666,443 | 5/1987 | Portner . |
| 4,955,856 | 9/1990 | Phillips . |
| 4,985,014 | 1/1991 | Orejola . |
| 4,995,857 | 2/1991 | Arnold . |
| 5,044,901 | 9/1991 | Fumero . |
| 5,383,839 | 1/1995 | Bohls ................. 600/16 |

Primary Examiner—William E. Kamm
Assistant Examiner—Scott M. Getzow
Attorney, Agent, or Firm—Brady, O'Boyle & Gates

[57] ABSTRACT

A biventricular pulsatile cardiac support system having a mechanically balanced stroke volume wherein a pair of side-by-side, valveless, compressible conduits extend through the compression chamber of a pulsatile flow cardiopulmonary bypass pump and a passive exterior valve positioned at the inlet and the outlet of the pump. The inlets of the conduits communicate with the right and left atria of the patient's heart and the outlets of the conduits communicate with the pulmonary artery and aorta so that the volume of blood passing from the right atrium, through the right ventricle, to the pulmonary artery, is substantially balanced with the volume of blood passing from the left atrium through the left ventricle to the aorta. The support system can be operated in single or biventricular support mode and in partial or total cardiopulmonary bypass mode, omitting the oxygenator used in conventional cardiopulmonary bypass, and in so doing, rely on the patient's own lungs rather than artificial oxygenator. This variant of cardiopulmonary support for cardiac surgery should reduce cost and complications associated with conventional cardiopulmonary bypass.

2 Claims, 4 Drawing Sheets

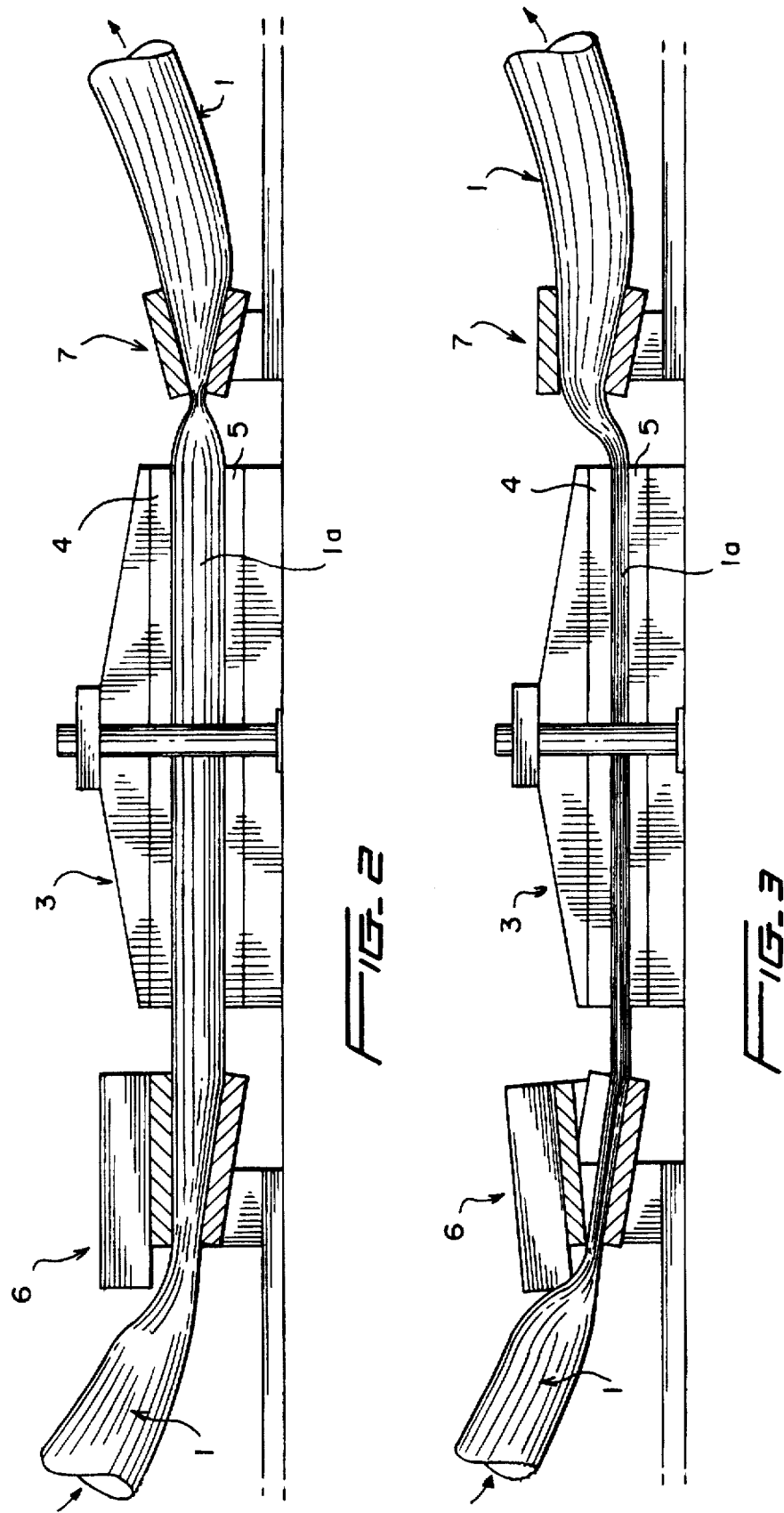

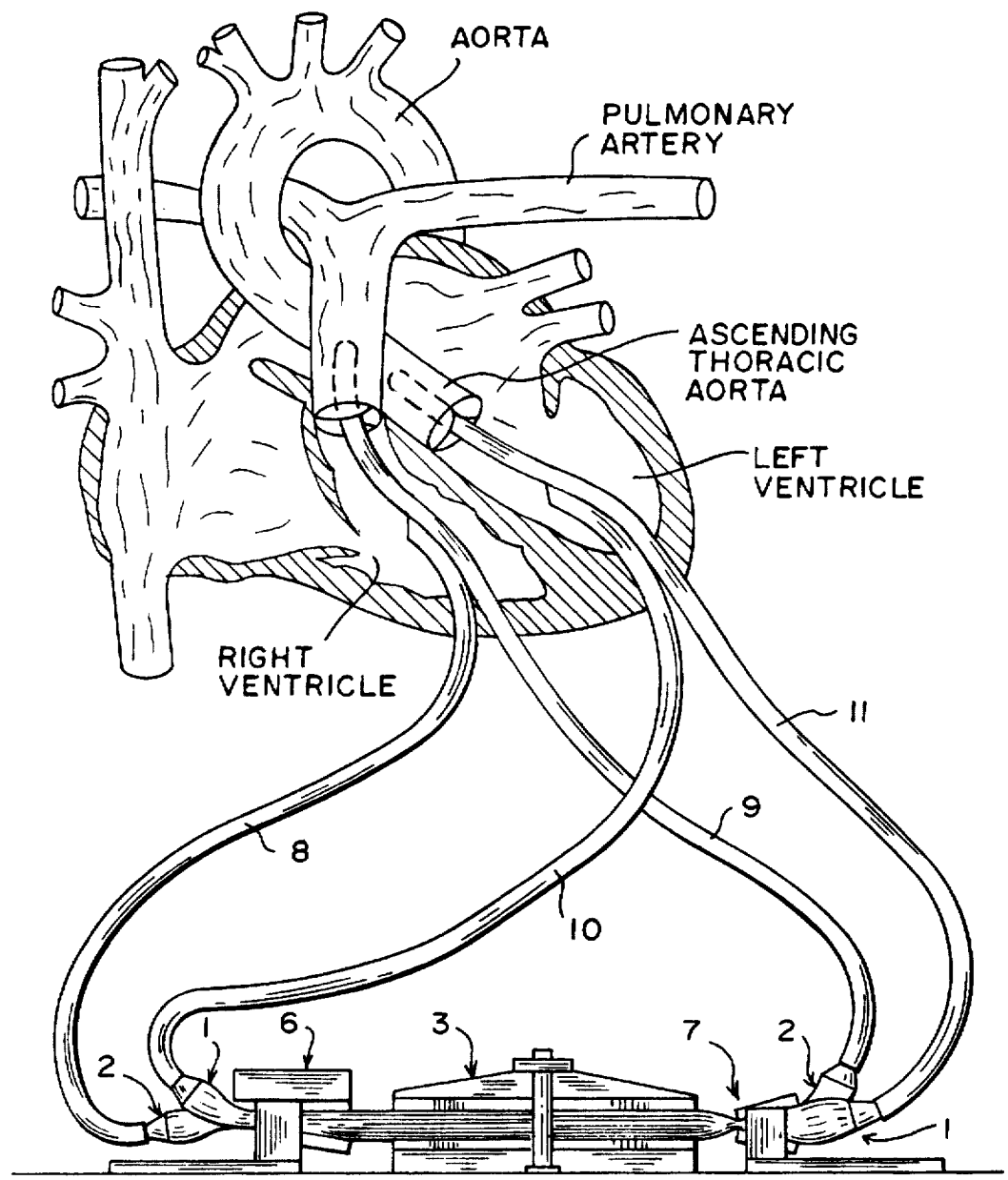
FIG_5

BIVENTRICULAR PULSATILE CARDIAC SUPPORT SYSTEM HAVING A MECHANICALLY BALANCED STROKE VOLUME

BACKGROUND OF THE INVENTION

In the human cardiovascular system, the volume of blood passing from the right atrium via the right ventricle to the pulmonary artery should be balanced on a beat-to-beat basis with the volume of blood passing from the left atrium via the left ventricle to the aorta. These volumes of blood are rarely balanced, when one or the other ventricle is malfunctioning or failing. If the ventricles do not automatically balance their output over a series of beats, severe right or left sided heart failure occurs and the patient will die.

Various biventricular circulatory assist systems have been proposed wherein a pair of pumps are individually controlled for balancing the outputs of the ventricles and elaborate electronic balancing mechanisms are employed for equalizing the outputs. These systems are very expensive and complex and, therefore, susceptible to failure while in use, and require sophisticated control mechanisms to prevent dysfunction.

After considerable research and experimentation, the biventricular pulsatile cardiac support system of the present invention has been devised which is simpler, more reliable and less expensive than heretofore employed systems.

SUMMARY OF THE INVENTION

The biventricular pulsatile cardiac support system of the present invention comprises, essentially, a pulsatile flow cardiopulmonary bypass pump having a pair of side-by-side valveless, compressible conduits extending through the compression chamber of the pump, and under the compression plate positioned therein. Exterior valves are provided at the inlet and outlet of the compressible conduits for controlling blood flow through the conduits. The inlet of one of the conduits communicates with the patient's right atrium, and the outlet of this conduit communicates with the patient's pulmonary artery. The inlet of the other conduit communicates directly with the patient's left atrium or indirectly via the left ventricle, and the outlet of this conduit communicates with the patient's ascending thoracic aorta. By this construction and arrangement, the volume of blood passing from the right atrium, through the right ventricle to the pulmonary artery is substantially balanced with the volume of blood passing from the left atrium through the left ventricle to the aorta, whereby either right or left-sided circulatory loads becoming significantly greater than the other are precluded.

BRIEF DESCRIPTION OF THE DRAWINGS

FIG. 2 is a side elevational view showing the passive inlet valve in the open position and the outlet valve in the closed position during the filling of the conduits;

FIG. 3 is a side elevational view showing the inlet valve in the closed position and the outlet valve in the open position during the compression stroke of the pump;

FIGS. 4 and 5 are diagrammatic views of the apparatus illustrated in FIGS. 1 to 3 set up for biventricular pulsatile cardiac support.

DESCRIPTION OF THE PREFERRED EMBODIMENT

Figure 1:
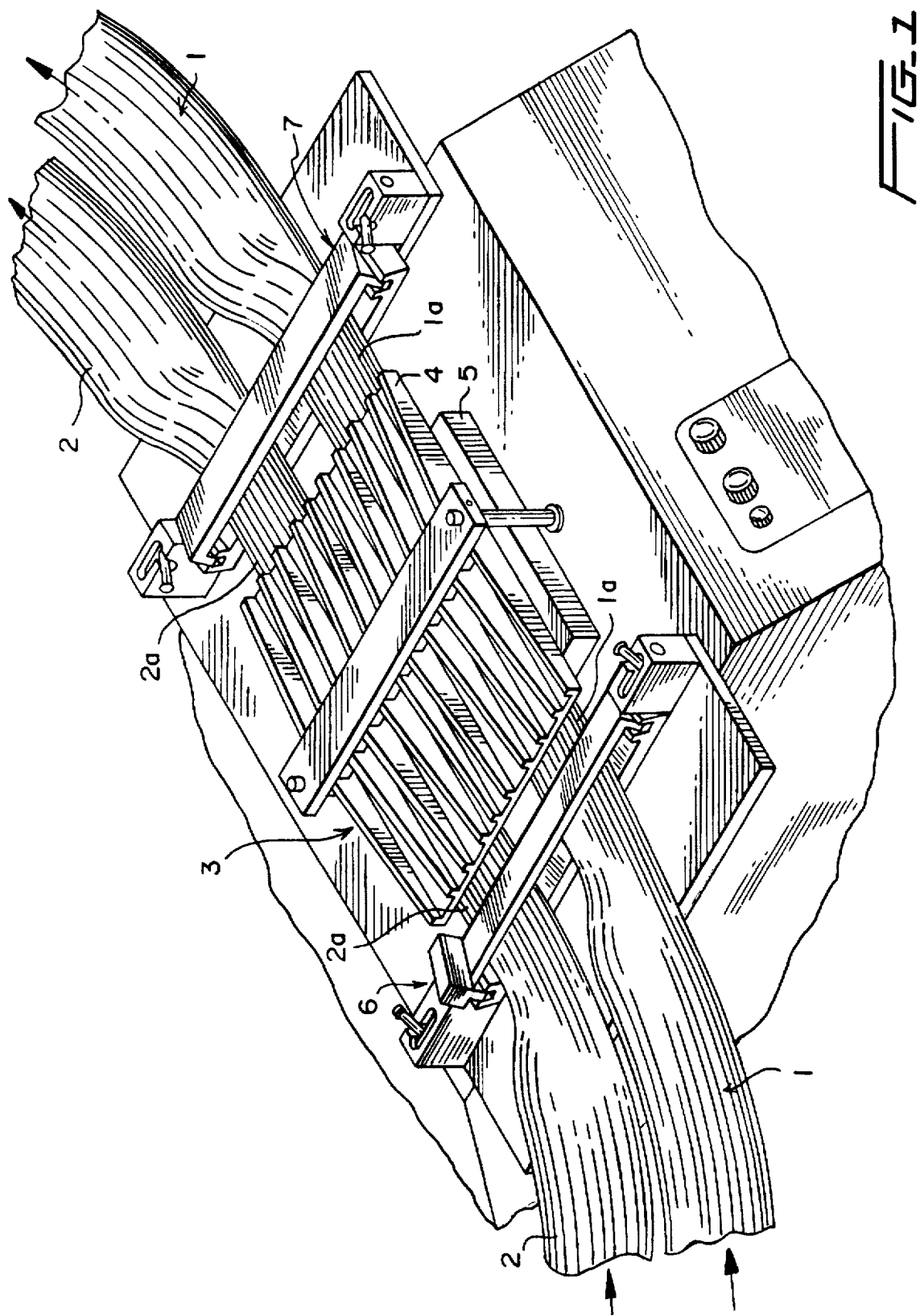
FIG. 1 is a fragmentary perspective view showing a pair of side-by-side, valveless compressible conduits extending through the compression chamber of a pulsatile flow cardiopulmonary bypass pump, and exterior, passive inlet and outlet valves.

Referring to the drawings and more particularly to FIG. 1, the biventricular pulsatile cardiac support system with mechanically balanced stroke volume of the present invention comprises, a pair of side-by-side valveless compressible conduits 1 and 2 extending through the compression chamber of a pulsatile flow cardiopulmonary bypass pump 3 of the type disclosed in U.S. Pat. Nos. 4,143,425 dated Mar. 13, 1979, and 4,293,961 dated Oct. 13, 1981, the description of which is incorporated herein by reference, which includes a movable compression plate 4 and a fixed plate 5. The conduits 1 and 2 also extend through passive, automatic plate valves 6 and 7 of the type disclosed in pending application Ser. No. 08/103,810, filed Aug. 10, 1993, now U.S. Pat. No. 5,383,839 dated Jan. 29, 1995, the description of which is incorporated herein by reference, wherein valve 6 is positioned in proximity to the inlet side of the pump 3, and valve 7 is similarly positioned at the outlet side of the pump 3. The portions of the compressible conduits 1 and 2 between the inlet and outlet valves form sacks 1a, 2a.

By the construction and arrangement of the compressible conduits 1 and 2 extending through the pump 3 and associated valves 6 and 7, as will be seen in FIG. 2, when there is no compression on the compressible conduits 1 and 2 by the pump compression plate 4, the inlet valve 6 is in the open position allowing blood to flow into the conduits 1 and 2, and the outlet valve 7 is in the closed position to prevent the flow of blood from the conduits 1 and 2, whereby blood flowing into the conduits pushes the compression plate 4 upwardly until the sacks 1a and 2a are filled. The drive mechanism of the pump 3 is such that plate 4 will not descend to compress the sacks 1a and 2a, as shown in FIG. 1, until the sacks 1a, 2a are filled, whereupon the inlet valve 6 is pivoted to the closed position and the outlet valve 7 is pivoted to the open position to allow blood to flow from the sacks 1a and 2a. As the pump compression plate 4 once again ascends to the initial position, the outlet valve 7 is pivoted to the closed position and the inlet valve 6 is pivoted to the open position.

Figure 4:
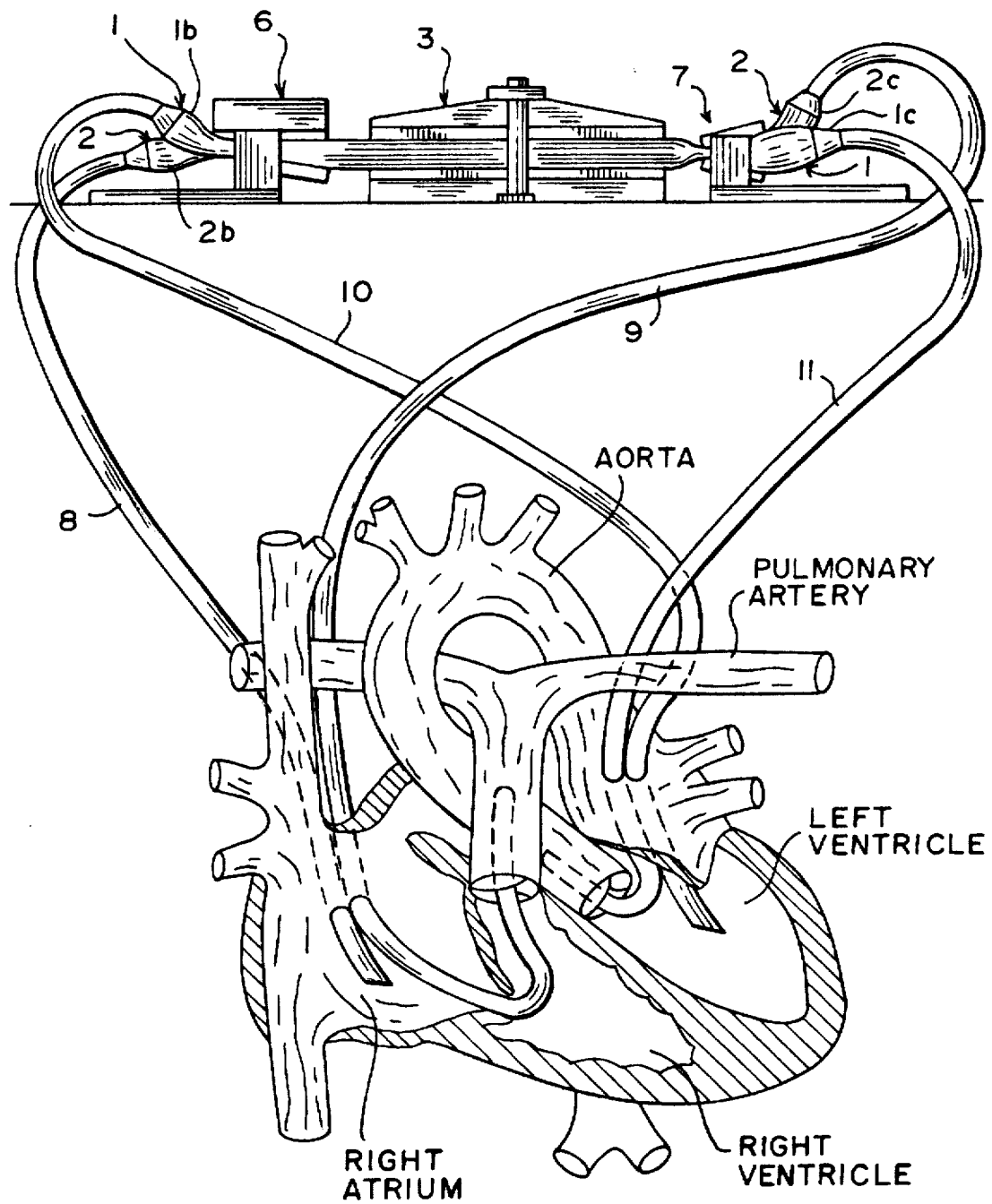

The biventricular circulatory assist system of the present invention is illustrated in FIG. 4 wherein the inlet 2b of compressible tube 2 is connected to a tube 8 communicating with the right atrium of the patient's heart, and the outlet 2c of the compressible tube 2 is connected to a tube 9 communicating with the pulmonary artery. The inlet 1b of compressible conduit 1 is connected to a tube 10 communicating with the left ventricle, and the outlet 1c of the conduit 1 is connected to a tube 11 communicating with the ascending thoracic aorta.

By the construction and arrangement of the side-by-side compressible conduits 1 and 2, the pulsatile flow cardiopulmonary bypass pump 3, and exterior valves 6 and 7, the volume of blood passing from the right atrium via the right ventricle to the pulmonary artery via tubes 8 and 9 is automatically balanced on a beat-to-beat basis with the volume of blood passing from the left atrium via the left ventricle to the aorta via tubes 10 and 11. This is accomplished due to the fact that when the inlet valve 6 is open, the outlet valve 7 is closed so that the blood flowing through the inlets 1b, 2b fills the sacks 1a, 2a, thereby pushing the pump compression plate 4 upwardly as shown in FIG. 2. The drive mechanism of the pulsatile pump 3 is such that the compression stroke of the pump will not commence until either sack 1a or 2a is filled, whereupon the compression plate 4 descends to pump the blood out of the sacks 1a, 2a simultaneously while the inlet valve 6 moves to the closed position and the outlet valve 7 moves to the open position, whereby the pumping rate is automatically varied as a function of the filling pressure.

While FIG. 4 shows the inlets of tubes 8 and 10 communicating with the right atrium and left ventricle, respectively, FIG. 5 illustrates another arrangement wherein the inlets of tubes 8 and 10 communicate with the right ventricle and left atrium, respectively. The preferred connection for most surgeons will be from the right atrium to the pulmonary artery, and from the left atrium to the aorta.

From the above description, it will be appreciated by those skilled in the art that the biventricular cardiac support system of the present invention provides an automatic balancing of output as a function of filling pressure, and which can, if desired, automatically vary its pumping rate as a function of filling pressure or, alternatively, can be made to synchronize its pumping rate in relation to intrinsic patient cardiac rate. The use of passive valves precludes the need for electronics, and the system can be operated in biventricular mode, or right ventricular or left ventricular mode alone.

Furthermore, the system of the present invention can be substituted for conventional cardiopulmonary bypass hardware omitting the conventional oxygenator and relying instead upon the patient's own lungs.

It is to be understood that the form of the invention herewith shown and described is to be taken as a preferred example of the same, and that various changes in the shape, size and arrangement of parts may be resorted to, without departing from the spirit of the invention or scope of the subjoined claims.

I claim:

1. A biventricular pulsatile cardiac support system having a mechanically balanced stroke volume comprising, a pulsatile flow cardiopulmonary bypass pump having a compression chamber intermediate the inlet and outlet of said pump, said compression chamber including a movable compression plate and a fixed plate, a pair of side-by-side, externally valved, compressible conduits extending through said compression chamber and under said compression plate, each conduit having an inlet and an outlet, a passive exterior valve positioned at the pump inlet and outlet, said pair of side-by-side conduits extending through said valves, the portions of said compressible conduits extending between the inlet and outlet valves forming sacks, the valve at the pump inlet being positioned downstream from the inlets of said conduits, the valve at the pump outlet being positioned upstream from the outlets of said conduits, a first tube having one end connected to the inlet of one of said conduits and an opposite end adapted to be connected to the right atrium of a patient's heart, a second tube having one end connected to the outlet of said one conduit and an opposite end adapted to be connected to the pulmonary artery of said patient, a third tube having one end connected to the inlet of the other of said conduits and an opposite end adapted to be connected to the left ventricle of the patient's heart, and a fourth tube having one end connected to the outlet of said other conduit and an opposite end adapted to be connected to the patient's aorta, whereby when the inlet valve is open and the outlet valve is closed blood flowing through the inlets of the side-by-side conduits fills the sack portions of the conduits underneath the pump compression plate, to thereby push the compression plate upwardly until at least one of the sacks is filled, whereupon the compression plate descends to compress the sacks, thereby pumping the blood out of the conduits simultaneously while the inlet valve moves to the closed position and the outlet valve moves to the open position, whereby the pumping rate is automatically varied as a function of the filling pressure, to thereby substantially balance the volume of blood passing from the right atrium to the pulmonary artery with the volume of blood passing from the left ventricle to the aorta.

2. A biventricular pulsatile cardiac support system having a mechanically balanced stroke volume comprising, a pulsatile flow cardiopulmonary bypass pump having a compression chamber intermediate the inlet and outlet of said pump, said compression chamber including a movable compression plate and a fixed plate, a pair of side-by-side, externally valved, compressible conduits extending through said compression chamber and under said compression plate, each conduit having an inlet and an outlet, a passive exterior valve positioned at the pump inlet and outlet, said pair of side-by-side conduits extending through said valves, the portions of said compressible conduits extending between the inlet and outlet valves forming sacks, the valve at the pump inlet being positioned downstream from the inlets of said conduits, the valve at the pump outlet being positioned upstream from the outlets of said conduits, a first tube having one end connected to the inlet of one of said conduits and an opposite end connected to the right ventricle of a patient's heart, a second tube having one end connected to the outlet of said one conduit and the opposite end adapted to be connected to the pulmonary artery of the patient's heart, a third tube having one end connected to the inlet of the other of said conduits and an opposite end adapted to be connected to the left atrium of said patient and a fourth tube having one end connected to the outlet of said other tube and an opposite end adapted to be connected to the patient's aorta, whereby when the inlet valve is open and the outlet valve is closed blood flowing through the inlets of the side-by-side conduits fills the sack portions of the conduits underneath the pump compression plate, to thereby push the compression plate upwardly until the sack portions are filled, whereupon the compression plate descends to compress the sacks, thereby pumping blood out of the conduits simultaneously while the inlet valve moves to the closed position and the outlet valve moves to the open position, whereby the pumping rate is automatically varied as a function of the filling pressure, to thereby substantially balance the volume of blood passing from the right ventricle to the pulmonary artery with the volume of blood passing from the left atrium to the aorta.

* * * * *